United States Patent [19]

Iida

[11] Patent Number: 5,057,317
[45] Date of Patent: Oct. 15, 1991

[54] SLOW-RELEASE PHARMACEUTICAL AGENT

[75] Inventor: Yoshimitsu Iida, Saitama, Japan

[73] Assignee: Chugai Seiyaku Kabushiki Kaisha, Tokyo, Japan

[21] Appl. No.: 171,817

[22] Filed: Mar. 22, 1988

[30] Foreign Application Priority Data

Mar. 24, 1987 [JP] Japan .................................. 62-69677

[51] Int. Cl.$^5$ .......................... A61K 9/00; A61K 9/24; A61K 9/26; A61K 9/54
[52] U.S. Cl. .................................... 424/423; 424/461; 424/470; 424/472; 424/474; 424/480; 424/490; 424/499
[58] Field of Search ............... 424/472, 499, 491, 422, 424/460, 468, 461, 479, 493, 477, 465, 423, 470, 474, 480

[56] References Cited

U.S. PATENT DOCUMENTS

| | | | |
|---|---|---|---|
| 2,753,288 | 7/1956 | Visscher | 424/477 |
| 3,477,864 | 11/1969 | Tuji | 424/491 X |
| 3,541,201 | 11/1970 | Brown | 424/491 X |
| 3,786,123 | 1/1974 | Katzen | 424/491 X |
| 4,361,546 | 11/1982 | Stricker et al. | 424/499 X |
| 4,457,907 | 7/1984 | Porter | 424/491 X |
| 4,695,591 | 9/1987 | Hanna et al. | 424/499 X |
| 4,753,804 | 6/1988 | Iaccheri et al. | 424/499 X |
| 4,843,071 | 6/1989 | Hohenwarter | 424/465 X |
| 4,863,741 | 9/1989 | Becker | 424/465 |

FOREIGN PATENT DOCUMENTS

| | | |
|---|---|---|
| 0218148 | 9/1985 | European Pat. Off. . |
| 2145555 | 2/1973 | France . |
| 2262023 | 9/1975 | France . |
| 58/035110 | 3/1983 | Japan .................................. 424/491 |
| 1155036 | 6/1969 | United Kingdom . |

OTHER PUBLICATIONS

M. Nakano et al., J. Pharm. Sci., 72, 378, 1983 "Sustained Release of Theophylline from Hydroxypropylcellulose Tablets".
G. Kallstrand et al., J. Pharm. Sci., 72, 772, 1983 "Membrane-Coated Tablets: A System for the Controlled Release of Drugs".
S. S. Jambhekar et al., J. Pharm. Sci., 74, 991, 1985 "pH-and Flow-Rate-Independent Release of Drug from Uncoated Slow-Release Tablets".

Primary Examiner—Thurman K. Page
Attorney, Agent, or Firm—Browdy and Neimark

[57] ABSTRACT

Slow-release pharmaceutical agents which comprise at least one adenine, cystine and tyrosine in combination with at least one pharmaecutically active substance are disclosed. The slow-release pharmaceutical agents which may be tablet, granule, implant, capsule, troche, etc., can either slowly release their active substances over time or release the active substances a predetermined time after their administration. And the slow-release pharmaceutical agent may be used with practically all types of drugs irrespective of whether they are water-soluble or slightly water-soluble, including hypotensives, antipyretic analgesic antiinflammatories, immunoregulators, adrenocortical hormones, antidiabetic agent, vasodilators, cardiotonics, antiarrhythmic agents, anti-arteriosclerotic agents, and antidotes.

18 Claims, 11 Drawing Sheets

—○— TABLETS PREPARED IN EXAMPLE 2
--○-- TABLETS PREPARED IN COMPARATIVE EXAMPLE

SLOW-RELEASE PHARMACEUTICAL AGENT

BACKGROUND OF THE INVENTION

While many compounds are known to be useful as pharmacologically active substances, some of them have relatively short biological half lives and must be administered several times a day in order for their full action to be exhibited. However, a decrease in the number of administrations will not only reduce the burden on the patient but will also increase his compliance and thus provide greater therapeutic effects. In order to meet this requirement, medicines must release their active ingredients slowly so that they maintain effective levels in the blood for a prolonged period of time. In addition, if the active substance of a drug can be released a predetermined time after its administration, it becomes possible to allow a larger amount of the active substance to be released at a particular site of an organ such as a digestive tract, thereby producing enhanced therapeutic effects.

Therefore, the principal object of the present invention is to provide a pharmaceutical agent which is so designed that it will either slowly release its active substance over time or release the active substance a predetermined time after its administration.

Various techniques have been proposed for preparing slow-release pharmaceutical agents that are capable of retaining the concentrations of their active substances in the blood for a prolonged period of time. Most of the slow-release pharmaceuticals so far proposed employ a variety of high-molecular weight materials which include: hydroxypropyl cellulose, hydroxypropyl methyl cellulose, hydroxypropyl methyl cellulose phthalate, pullulan, gelatin, collagen, casein, agar, gum arabic, dextrin, ethyl cellulose, methyl cellulose, chitin, chitosan, mannan, carboxymethylethyl cellulose, sodium carboxymethyl cellulose, polyethylene glycol, sodium alginate, poly(vinyl alcohol), cellulose acetate, poly(vinylpyrrolidone), silicone, poly(vinyl acetal) diethylamino acetate and albumin [see Sustained and Controlled Release Drug Delivery Systems, Marcel Dekker, Inc., 1978; Yakkyoku (Pharmacy), vol. 35, No. 2, pp 575-583, 1984; and Japanese Patent Public Disclosure No. 62521/1984].

The use of the above-listed high-molecular weight materials in manufacturing slow-release pharmaceuticals involves several problems: (1) many high-molecular weight materials, particularly those which are soluble in water, have such a high moisture content that the pharmacologically active substances incorporated therein are liable to suffer decomposition, such as by hydrolysis, and often fail to withstand prolonged storage; (2) high-molecular weight material have certain distributions in molecular weight and their molecular weight distribution and average molecular weight generally differ from one to another notwithstanding the existence of certain limits to be complied with and, therefore, the slow-release pharmaceuticals employing such high-molecular weight materials will experience considerable variations in drug dissolution rate no matter how strict the quality control is during the manufacturing process; (3) some of the slow-release pharmaceuticals employing high-molecular weight materials are used in the state of being implanted in the human body, but many high-molecular weight materials are not decomposed in the human body at all or are decomposed only slightly, so they must be removed from the human body after they have liberated the pharmaceutically active substance; even the high-molecular weight materials that are decomposable in the human body are in most cases dependent upon the presence of decomposition enzymes if the rate of their decomposition is to be satisfactory, and this also holds for the rate of release of the active substance; furthermore, even the decomposable high-molecular weight materials are not completely decomposed to monomers and there is a high possibility that only a part of them will be decomposed, most of them remaining as polymers and being absorbed by tissues to become a potential antigen that can cause an anaphylactic shock [see Seiyaku Kogyo (Pharmaceutical Factory), vol 3, No. 10, pp. 552-557 (1983); and Kagaku no Ryoiki (Region of Chemistry), Special Issue, No. 134, pp. 151-157, Nankodo]; (4) in slow-release pharmaceuticals of the matrix type and those wherein the active substances (i.e., drugs) are released through a semipermeable membrane, the drug release rate is so highly dependent on the solubility of the drug that such types of slow-release pharmaceuticals are not suitable for use with sparingly soluble drugs; and (5) pharmaceuticals having coatings of water-insoluble high-molecular weight substances are unable to release the active substance a predetermined time after their administration; water-soluble high-molecular weight substances will immediately swell by an infinite degree and are unable to inhibit the drug release for a prolonged period; enteric high-molecular weight substances are unable to release the drug at pHs below 5.0-5.5 but will immediately release it at higher pHs, and hence are unable to perform time-dependent, not pH-dependent, control of the drug release.

The present inventors conducted various studies in order to develop a process for preparing a slow-release pharmaceutical agent that is free from the aforementioned problems of the prior art products. As a result, the present inventors unexpectedly found that the duration of the sustained release of a pharmaceutically active substance can be extended or its release a predetermined time after drug administration can be realized by employing at least one "slow-release rendering additive" selected from the group consisting of adenine, cystine and tyrosine, all being low-molecular weight substances. Cystine and tyrosine occur in isomeric forms but their effectiveness is independent of whether they are in D-, L- or DL-form

DETAILED DESCRIPTION OF THE INVENTION

The slow-release pharmaceutical agent of the present invention is prepared by the following procedure: predetermined amounts of a pharmaceutically active substance and an excipient are weighed; a predetermined amount of a selected "slow-release rendering additive" is weighed; and the individual components are mixed by a routine method. The amount of the pharmaceutically active substance used varies with such factors as the type and dosage form of the pharmaceutical agent and is usually less than 90%, preferably less than 75%, of the total weight of the composition. The amount of the "slow-release rendering" additive to be incorporated is usually more than 2%, preferably more than 5%, of the total weight of the composition.

The use of an excipient is optional but if it is to be used, preferable excipients are lactose, mannitol, inositol, calcium citrate, dibasic calcium phosphate, fumaric acid, hardened oils, corn oil, sesame oil, stearic acid, etc. The amount of excipient, if one is to be used at all in combination with the "slow-release rendering" additive is usually in the range of from 0 to 95%, preferably from 0 to 80%, of the total weight of the composition.

The slow-release pharmaceutical agent of the present invention may be used with practically all types of drugs irrespective of whether they are water-soluble or slightly water-soluble, including hypotensives, antipyretic analgesic antiinflammatories, immunoregulators, adrenocortical hormones, antidiabetic agents, vasodilators, cardiotonics, antiarrhythmic agents, anti-arteriosclerotic agents and antidotes.

The term "slightly water-soluble" when applied to drugs means that their water solubility affects their absorption by the human body. With slightly soluble drugs that have water solubilities of no more than 0.1% [Nakai and Hanano, "Seizaigaku (Pharmaceutics)", p. 296, Sep. 20, 1974, Nanzando], good slow-releasing effects can be attained by grinding the drugs to particles having an average size of no more than 10 $\mu$m and with hydroxypropyl cellulose of low substitution degree and hydroxypropyl cellulose being used as excipients. Drug particles having an average size of no more than 10 $\mu$m can be prepared by using a jet mill grinder (Model FS-4 of Seishin Enterprise Co., Ltd.).

To the mixed powder thus prepared and which contains the pharmaceutically active substance, a "slow-release rendering" additive and optionally an excipient, a lubricant such as magnesium stearate, calcium stearate or talc, and any other necessary components are added and the resulting mixture is compressed into tablets. If desired, the mixture may be worked into a dosage form suitable for implanting in the human body.

The mixed powder may also be blended with sucrose, a fragrance, a colorant and any other appropriate components and the resulting blend is then compressed to form troches of predetermined phases. If desired, the blend may be formulated as a pharmaceutical for buccal administration.

A layer (A) containing a pharmaceutically active substance may be placed on another layer (B) containing no such active substance and the two layers are then compressed together to form a double-layered tablet which achieves enhanced delivery of the effective substance after a given period of time has passed. Two modifications of this multiple-layered tablet are as follow: a tablet which is prepared by compressing a layer having the composition specified by the present invention and a fast-release layer containing the same pharmaceutically active substance; and a tablet prepared by compressing the following three layers together, the first layer having the composition specified by the present invention, the second layer containing at least one "slow-release rendering" additive, and the third layer being a fast-release layer containing a pharmaceutically active substance which is the same as what is present in the first layer.

The mixed powder described above may be blended with an appropriate binder, such as hydroxypropyl cellulose, hydroxypropyl methyl cellulose or cornstarch, dissolved in either water or an organic solvent, and the blend is granulated, dried and classified to obtain granules. If desired, a granulation having this composition may be mixed with a fast-release granulation containing the same pharmaceutically active substance. Slow-release enteric granules may be prepared by coating the first granulation with enteric bases such as hydroxypropyl methyl cellulose phthalate and carboxymethylethyl cellulose. Said first granulation may be coated with water-insoluble bases and the so coated granules may optionally be mixed with fast-release granules containing the same pharmaceutically active substance. The fast-release granules containing a pharmaceutically active substance may be coated with at least one "slow-release rendering" additive to convert them into slow-release granules that release the drug predetermined time after their administration.

if desired, these slow-release granules may be compressed to form slow-release tablets; mixtures of said granules with water-insoluble bases may be compressed into tablets; and the so formed tablets may be coated with enteric bases or water-insoluble bases. These tablets may be provided with a sugar coating which may optionally contain a pharmaceutically active substance that is of the same type as incorporated in the center of the tablets. Core/shell type slow-release tablets may be prepared by compressing the aforementioned tablets after they have been coated with a fast-release composition containing the same pharmaceutically active substance. In this case, a coat of at least one "slow-release rendering" additive may be provided between the core tablet and the shell of the fast-release composition. The fast-release core tablet containing a pharmaceutically active substance may be coated first with a layer containing at least one "slow-release rendering" additive, then with an enteric base such as hydroxypropylmethyl cellulose phthalate or carboxymethylethyl cellulose to form an enteric tablet that releases the active substance a predetermined time after drug administration.

Any type of the aforementioned granules may be encapsulated to formulate capsules. If desired, the aforementioned slow-release granules may be incorporated in suppository bases to form slow-release suppositories. Alternatively, slow-release suppositories may be prepared by coating the aforementioned slow-release tablets with suppository bases.

The "slow-release rendering" additive to be incorporated in the slow-release pharmaceutical agent of the present invention may be used either independently or in admixtures of any appropriate proportions. By means of adding water-soluble materials such as lactose, mannitol and inositol, or compounds such as calcium citrate and dibasic calcium phosphate that are either water-soluble or highly wettable with water, the dissolution of a pharmaceutically active substance can be promoted. Conversely, the dissolution of the active substance can be retarded by adding oils such as corn oil and sesame oil or waxes such as hardened oils and stearic acid. The dissolution rate of the active substance can be varied with the pH of the environment of use by adding an enteric base such as hydroxypropylmethyl cellulose phthalate or carboxymethylethyl cellulose, or an organic acid such as fumaric acid. It is also possible to maintain a substantially constant dissolution rate at all pHs of the environment.

The slow-release pharmaceutical agent of the present invention releases its active substance as the "slow-release rendering" additive is slowly lost, so the pharmaceutically active substance that can be incorporated may be water-soluble or sparingly water-soluble and is not limited to any particular type.

It should of course be understood that in putting the slow-release pharmaceutical agent of the present invention to use, colorants, flavoring agents, stabilizers and any other appropriate additives may be added as required.

The present invention is hereunder described in greater detail with reference to working examples and a comparative example, to which the scope of the invention is by no means limited.

Example 1

| Layered tablet | lower layer (mg) | middle layer (mg) | upper layer (mg) |
|---|---|---|---|
| Nicorandil | 7 | — | 3 |
| Adenine | 52.6 | 29.8 | — |
| Lactose | — | — | 16.8 |
| Crystalline cellulose | — | — | 10 |
| Calcium stearate | 0.4 | 0.2 | 0.2 |
| Total | 60 | 30 | 30 |

Seven grams of Nicorandil, 52.6 g of adenine and 0.4 g of calcium stearate were weighed and mixed well in a polyethylene bag to form a mixed powder A.

In a separate step, 29.8 g of adenine and 0.2 g of calcium stearate were weighed and mixed well in a polyethylene bag to form a mixed powder B.

Thereafter, 3 g of Nicorandil, 16.8 g of lactose, 10 g of crystalline cellulose and 0.2 g of calcium stearate were weighed and mixed well in a polyethylene bag to form a mixed powder C.

Multilayer tableting was performed on a single-punch machine equipped with a die (7 mm$^\phi$) and flat-faced punches: first, 60 mg of the mixed powder A was placed in the die and precompressed lightly; 30 mg of the mixed powder B was placed on the first fill and lightly precompressed; thereafter, 30 mg of the mixed powder C was placed on the second fill and compressed with a total pressure of about 1 ton.

Figure 1:
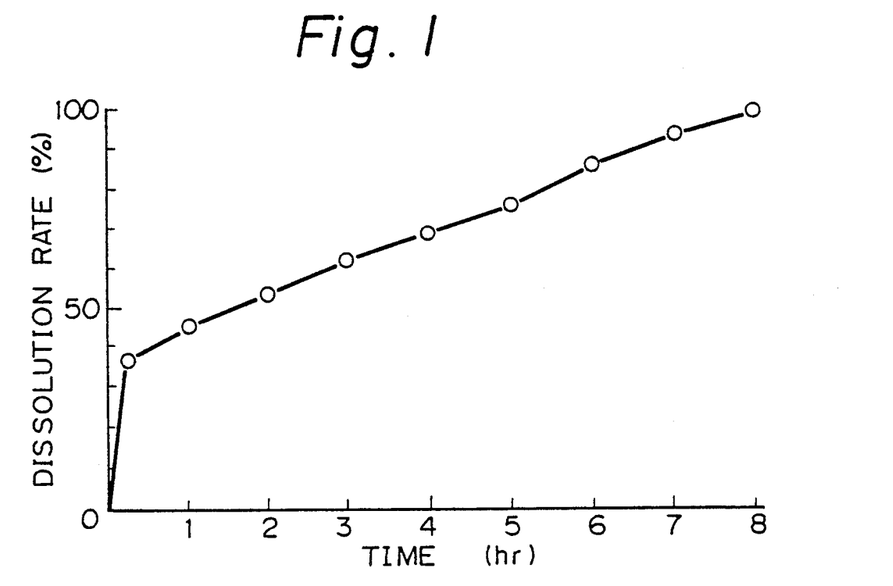
FIG. 1 depicts the dissolution profile of the layered tablets prepared in Example 1.

The resulting multiple-layered tablets had the dissolution profile depicted in FIG. 1 that was obtained by conducting a dissolution test with an apparatus of the type specified in "Method I (rotary basket method)", the Japanese Pharmacopoeia, 11th rev.; 500 ml of Fluid 2 (pH≃6.8) was used as a testing fluid and the basket was rotated at 100 rpm.

Example 2

| Tablet | |
|---|---|
| Thiamazole | 5 (mg) |
| L-tyrosine | 70 |
| Adenine | 70.5 |
| Cornstarch | 2.5 |
| Magnesium stearate | 2 |
| Total | 150 |

Seventy grams of L-tyrosine and 70.5 g of adenine were mixed well in a mortar to form a triturate, which was well blended with 20.8 g of 12% cornstarch paste. The blend was granulated after passage through a 35-mesh sieve, dried at 50° C. in a tray dryer for 5 hours and classified on a 32-mesh sieve to obtain a granulation. Five grams of Thiamazole, 143 g of the granulation and 2 g of magnesium stearate were weighed and mixed well in a polyethylene bag.

The mix was charged into a single-punch tableting machine equipped with a die (8 mm$^\phi$) and flat-faced punches, and compressed for a total pressure of 1.2 tons to make tablets each weighing 150 mg.

Comparative Example 1

| Tablet | |
|---|---|
| Thiamazole | 5 (mg) |
| Lactose | 121 |
| Crystalline cellulose | 20 |
| Cornstarch | 2 |
| Magnesium stearate | 2 |
| Total | 150 |

Lactose (121 g) and 12% cornstarch paste (16.7 g) were blended well in a mortar. The blend was granulated after passage through a 35-mesh sieve, dried at 50° C. in a tray dryer for 5 hours, and classified on a 32-mesh sieve to obtain a granulation. Five grams of Thiamazole, 123 g of the granulation, 20 g of crystalline cellulose and 2 g of magnesium stearate were weighed and mixed well in a polyethylene bag.

The mix was charged into a single-punch machine equipped with a die (8 mm$^\phi$) and flat-faced punches, and compressed for a total pressure of 1.2 tons to make tablets each weighing 150 mg.

Figure 2:
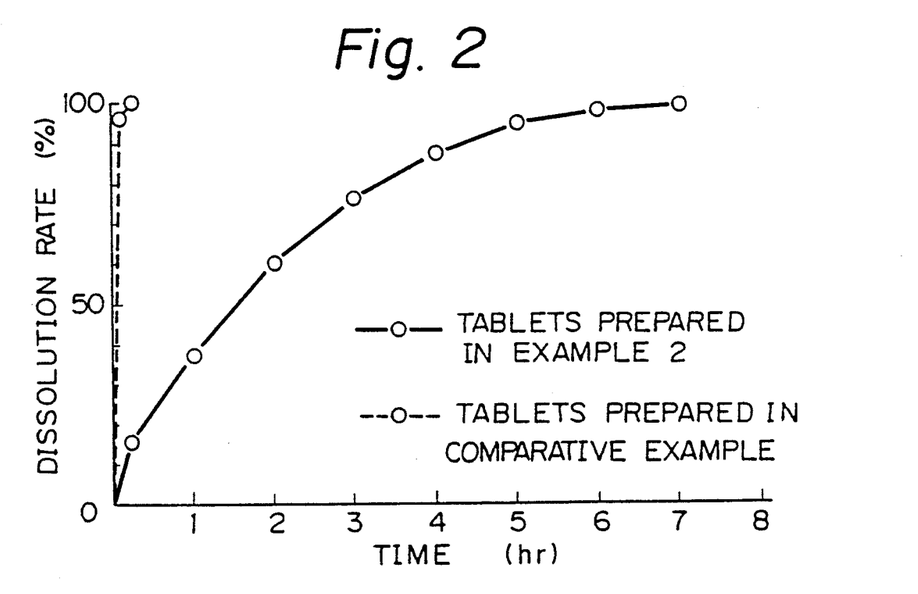
FIG. 2 depicts the dissolution profiles of the tablets prepared in Example 2 (—O—) and in Comparative Example 1 (—0—)

The tablets prepared in Example 2 and Comparative Example 1 had the dissolution profiles shown in FIG. 2. The data in FIG. 2 were obtained by conducting dissolution tests with an apparatus of the type shown in "Method II (puddle method) of Dissolution Test", the Japanese Pharmacopoeia, 11th rev.; 500 ml of Fluid 2 (pH≃6.8) was used as a testing fluid and the puddle was rotated at 100 rpm.

Example 3

| Granules (per 500 mg) | |
|---|---|
| Theophylline | 150 (mg) |
| DL-Cystine | 330 |
| Corn oil | 10 |
| Carboxymethyl cellulose | 10 |
| Total | 500 |

A hundred and fifty grams of Theophylline and 330 g of DL-cystine were weighed and mixed well in a mortar. To the resulting triturate, a mixture of 10 g of corn oil with 100 g of a 10% solution of carboxymethylethyl cellulose in ethanol was added and blended well. The blend was granulated in a rotary granulator equipped with a net (1.2 mm$^\phi$), dried at 45° C. in a tray dryer for 6 hours, and classified on a 10-mesh sieve to make granules.

Figure 3:
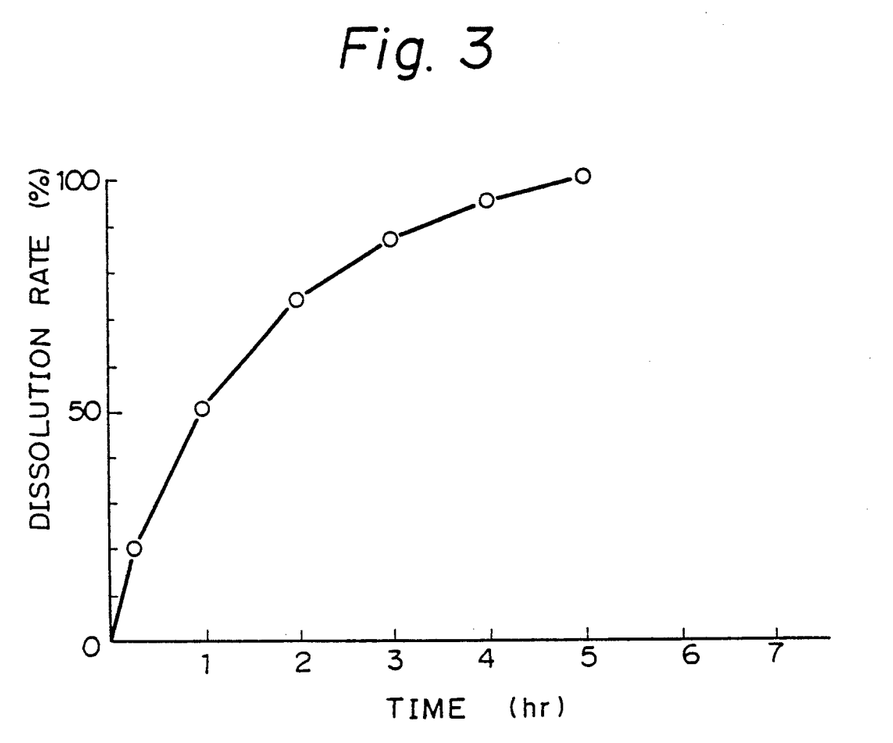
FIG. 3 depicts the dissolution profile of the granules prepared in Example 3.

The granules had the dissolution profile shown in FIG. 3 that was obtained by conducting a dissolution test on 200 mg of the granules with an apparatus of the type specified in "Method I (rotary basket method) of Dissolution Test", Japanese Pharmacopoeia, 11th rev.; 500 ml of Fluid I (pH≈1.2) was used as a testing fluid and the basket was rotated at 100 rpm.

Example 4

| Coated tablet | |
|---|---|
| Core tablet | |
| Picibanil ® (freeze-dried, powder: 5 KE) | 14 (mg) |
| Lactose | 31.5 |
| Hydroxypropyl cellulose of low substitution degree | 50 |
| Hydroxypropyl cellulose | 4 |
| Calcium stearate | 0.5 |
| Subtotal | 100 |
| Outer layer | |
| Adenine | 100 (mg) |
| L-Cystine | 50 |
| Dibasic calcium phosphate | 45 |
| Hydroxypropylmethyl cellulose | 4 |
| Calcium stearate | 1 |
| Subtotal | 200 |
| Enteric coating layer | |
| Eudragit ® L30D 55 (dried) | 30 (mg) |
| Triacetin | 3 |
| Talc | 7 |
| Subtotal | 40 |
| Total | 340 |

Fourteen grams of Picibanil ® (freeze-dried powder), 31.5 g of lactose and 50 g of hydroxypropyl cellulose of low substitution degree were weighed and mixed well in a mortar. To the triturate, 40 g of a 10% aqueous solution of hydroxypropyl cellulose was added and the individual components were blended together. The blend was sieved through a 16-mesh screen, granulated, dried by being left in a silica gel filled desiccator for one day, and classified on a 12-mesh sieve. The granulation (99.5 g) and calcium stearate (0.5 g) were mixed well in a polyethylene bag.

The mix was charged in a single-punch tableting machine equipped with a die (7 mm$^\phi$) and punches (R=10 mm), and compressed for a total pressure of 0.8 tons to make core tablets each weighing 100 mg.

A hundred grams of adenine, 50 g of L-cystine and 45 g of dibasic calcium phosphate were weighed and mixed well in a mortar. To the triturate, 40 g of a 10% aqueous solution of hydroxypropylmethyl cellulose was added and the individual components were blended together. The blend was sieved through a 20-mesh screen, granulated, dried at 50° C. in a tray dryer for 5 hours, and classified on a 16-mesh sieve. The granulation (199 g) and calcium stearate (1 g) were intimately mixed in a polyethylene bag to made granules for the outer layer.

A die (10 mm$^\phi$) and punches (R=14 mm) were set on a single-punch tableting machine and 70 mg of the granules for the outer layer were charged into the die. The core tablet was placed on the center of the granulation and another 130 mg of the granules for the outer layer was charged into the die. The charge was compressed for a total pressure of about 1.5 tons to make double-layered tablets.

Triacetin (3 g) and talc (7 g) were dissolved in 140 g of water under agitation. Thereafter, 100 g of Eugragit ® L3OD 55 (30% dispersion) was added to make an enteric coating solution.

Thirty grams of the double-layered tablets (ca. 100 in number) and 200 g of preliminarily prepared dummy tablets (9 mm$^\phi$, R=13 mm; weight of each tablet, 210 mg) were charged into a Flow Coater (UNI-GLATT of Okawara Mfg. Co., Ltd.) and a coating operation was performed by standard procedures until each of the double-layered tablets was coated with 40 mg of the previously prepared enteric coating solution.

The so prepared double-layered tablets with an enteric coat had the dissolution profiles shown in Table 1. The data in Table 1 was obtained by conducting a microbial release test on the tablets with an apparatus of the type specified in "Method II (puddle method) of Dissolution Test", Japanese Pharmacopoeia, 11th rev.; 500 ml each of Fluid 1 (pH≈1.2) and Fluid 2 (pH≈6.8) was used as testing fluids and the puddle was rotated at 100 rpm.

Microbial release was established by microscopic observation of the testing fluids.

TABLE 1

| Testing fluid | Time (hr) | | | | | |
|---|---|---|---|---|---|---|
| | 0.5 | 1 | 2 | 3 | 4 | 5 |
| I | − | − | − | − | − | − |
| II | − | − | − | − | + | + |

−: No visible microbial cells
+: Visible microbial cells

Example 5

| Layered tablet | upper layer (mg) | lower layer (mg) |
|---|---|---|
| Phenacetin | 50 | 100 |
| Lactose | 37 | — |
| Hydroxypropyl cellulose of low substitution degree | 10 | — |
| L-Tyrosine | — | 93 |
| Hydroxypropyl cellulose | 2 | 5 |
| Calcium stearate | 1 | 2 |
| Total | 100 | 200 |

Phenacetin and L-tyrosine were ground with a jet mill (Model FS-4 of Seishin Enterprise Co., Ltd.) into particles having an average size of 2–3 μm (the particles obtained by grinding with a jet mill are hereinafter referred to as "jet mill ground powder").

Fifty grams of Phenacetin (jet mill ground powder), 37 g of lactose and 10 g of hydroxypropyl cellulose of low substitution degree were weighed and mixed well in a mortar. To the triturate, 20 g of a 10% aqueous solution of hydroxypropyl cellulose and 12 g of water were added and blended well. The blend was ground after passage through a 14-mesh sieve, dried at 50° C. in a tray dryer for 5 hours, and classified on a 10-mesh sieve. To 99 g of the granulation, 1 g of calcium stearate was added and the two were mixed well in a polyethylene bag. The resulting granulation was designated granulation (a).

A hundred grams of Phenacetin (jet mill ground powder) and 93 g of L-tyrosine (jet mill ground powder) were weighed and mixed well in a mortar. To the triturate, 50 g of a 10% aqueous solution of hydroxypropyl cellulose and 44 g of water were added and blended well. The blend was granulated after passage through a 14-mesh sieve, dried at 50° C. in a tray dryer for 5 hours, and classified on a 10-mesh sieve. To 198 g of the granulation, 2 g of calcium stearate was added and the two were mixed well in a polyethylene bag. The resulting granulation was designated granulation (b).

Multi-layer tableting was performed on a single-punch machine equipped with a die (10 mm$^\phi$) and flat-faced punches: first, 200 mg of granulation (b) was placed in the die and precompressed lightly; then 100 mg of granulation (a) was placed on the first fill and compressed with a total pressure of about 2 tons.

Figure 4:
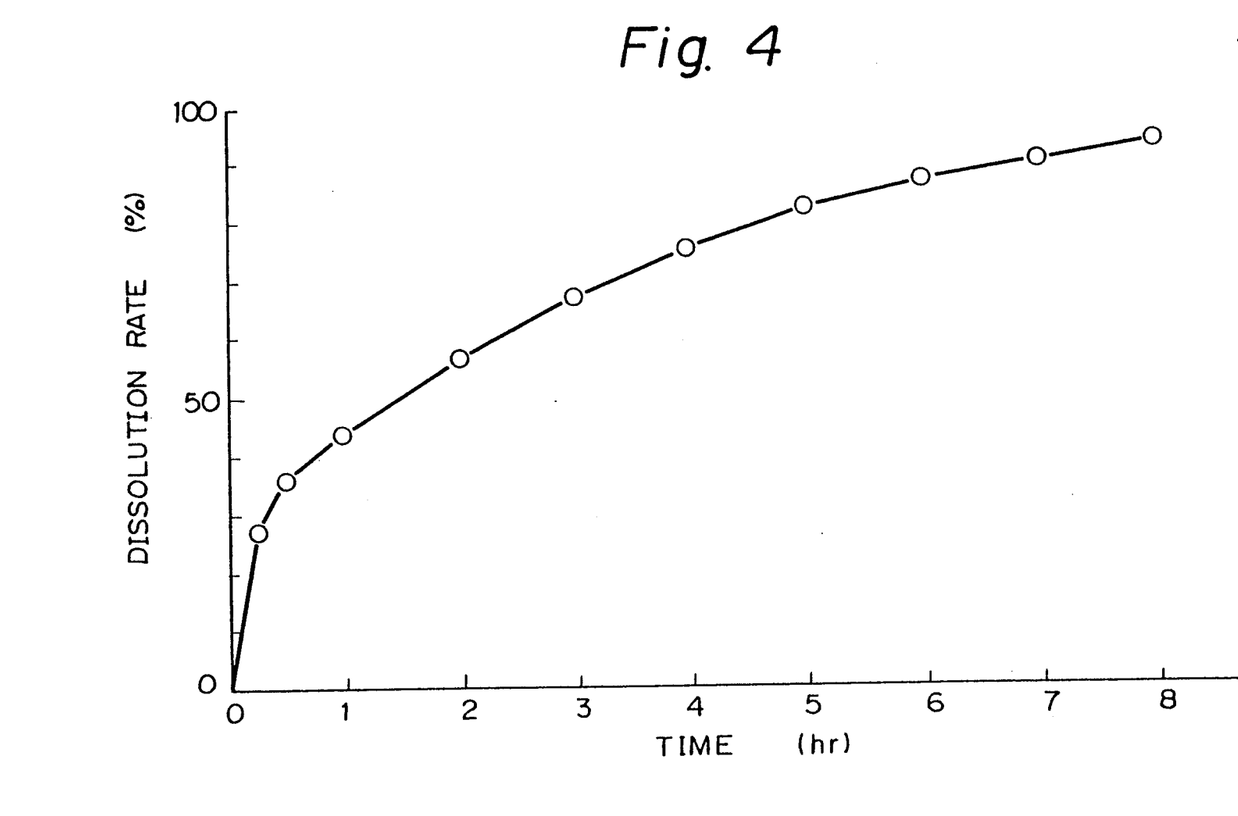
FIG. 4 depicts the dissolution profile of the layered tablets prepared in Example 5.

The resulting double-layered tablets had the dissolution profile depicted in FIG. 4 that was obtained by conducting a dissolution test with an apparatus of the type specified in "Method II (puddle method) of Dissolution Test", Japanese Pharmacopoeia, 11th rev.; 900 ml of distilled water was used as a testing fluid and the puddle was rotated at 100 rpm.

Example 6

| Tablet | |
|---|---|
| Griseofulvin | 125 (mg) |
| L-Tyrosine | 40 |
| Fumaric acid | 126 |
| Hydroxypropyl cellulose | 6 |
| Magnesium stearate | 3 |
| Total | 300 |

A hundred and twenty-five grams of griseofulvin (jet mill ground powder; average particle size, 1–2 μm), 40 g of L-tyrosine (jet mill ground powder; average particle size, 2–3 μm) and 126 g of fumaric acid (jet mill ground powder; average particle size, 4–5 μm) were weighed and mixed well in a mortar. To the triturate, 60 g of a 10% aqueous solution of hydroxypropyl cellulose and 62 g of water were added and blended well. The blend was granulated after passage through a 14-mesh sieve, dried at 60° C. in a tray dryer for 3 hours, and classified on a 10-mesh sieve to 297 g of the granulation, 3 g of magnesium stearate was added and the two were mixed well in a polyethylene bag.

The mix was charged into a single-punch tableting machine equipped with a die (10 mm$^\phi$) and flat-faced punches, and compressed for a total pressure of about 2 tons to make tablets each weighing 300 mg.

Comparative Example 2

| Tablet | |
|---|---|
| Griseofulvin | 125 (mg) |
| Lactose | 166 |
| Hydroxypropyl cellulose | 6 |
| Magnesium stearate | 3 |
| Total | 300 |

A hundred and twenty-five grams of griseofulvin (jet mill g round powder; average particle size, 1–2 μm) and 166 g of lactose were weighed and mixed well in a mortar. To the triturate, 60 g of a 10% aqueous solution of hydroxypropyl cellulose and 14 g of water were added and blended well. The blend was granulated after passage through a 14-mesh sieve, dried at 60° C. in a tray dryer for 3 hours, and classified on a 10-mesh sieve. To 297 g of the granulation, 3 g of magnesium stearate was added and the two were mixed well in a polyethylene bag.

The mix was charged into a single-punch tableting machine equipped with a die(10 mm$^\phi$) and flat-faced punches, and compressed for a total pressure of about 2 tons to make tablets each weighing 300 mg.

Figure 5:
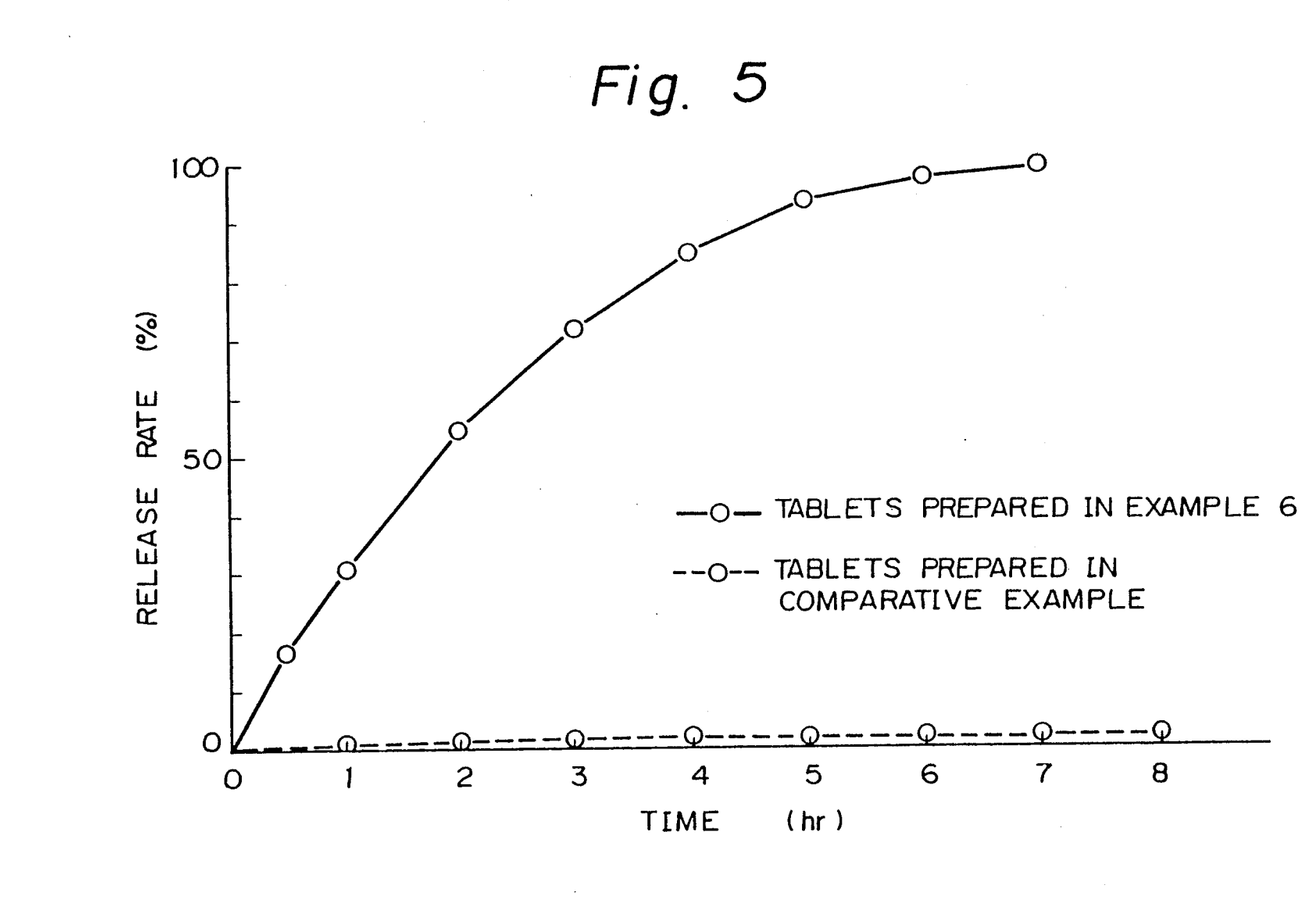
FIG. 5 depicts the drug release profiles of the tablets prepared in Example 6 (—O—) and Comparative Example 2 (—0—)

The tablets prepared in Example 6 and Comparative Example 2 had the drug release profiles shown in FIG. 5 (griseofulvin was insoluble in water, so the state of dispersion of its fine particles was evaluated by turbidity measurement). The data in FIG. 5 was obtained by conducting a release test with an apparatus of the type specified in the "Method of Disintegration Test", Japanese Pharmacopoeia, 11th rev.; 1,000 ml of distilled water was used as a testing fluid and the glass tubes containing the test fluid were moved up and down 20 times a minute.

Example 7

| Tablet | |
|---|---|
| Griseofulvin | 125 (mg) |
| L-Tyrosine | 166 |
| Hydroxypropyl cellulose | 6 |
| Magnesium stearate | 3 |
| Total | 300 |

A hundred and twenty-five grams of griseofulvin (jet mill ground powder; average particle size, 1–2 μm) and 166 g of L-tyrosine (jet mill ground powder; average particle size, 2–3 μm) were weighed and mixed well in a mortar. To the triturate, 60 g of a 10% aqueous solution of hydroxypropyl cellulose and 58 g of water were added and blended well. The blend was granulated after passage through a 14-mesh sieve, dried at 60° C. in a tray dryer for 3 hours, and classified on a 10-mesh sieve. To 297 g of the granulation, 3 g of magnesium stearate was added and the two were mixed well in a polyethylene bag.

The mix was charged into a single-punch tableting machine equipped with a die (10 mm$^\phi$) and flat-faced punches, and compressed for a total pressure of about 2 tons to make tablets each weighing 300 mg.

Figure 6:
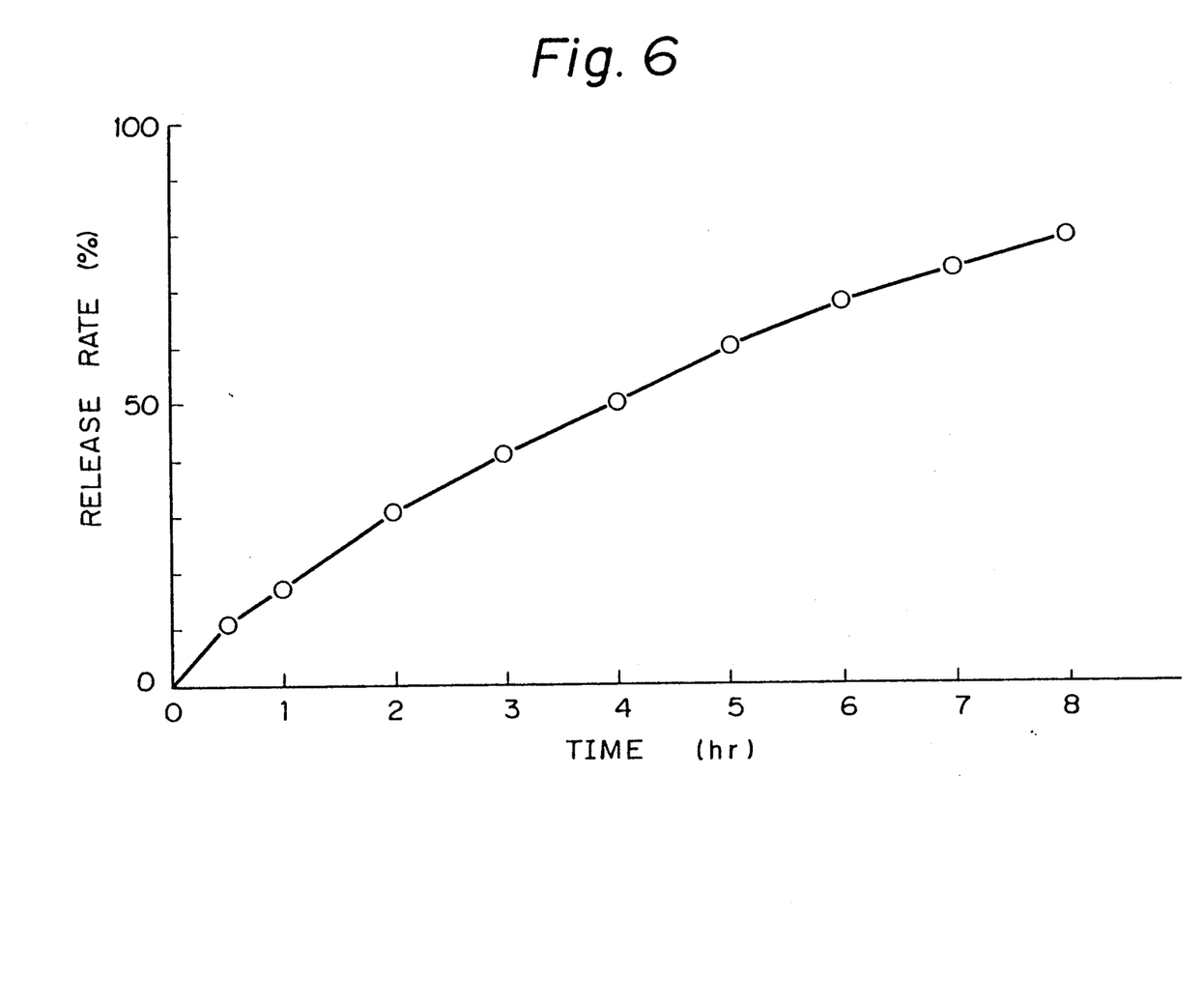
FIG. 6 depicts the drug release profile of the tablets prepared in Example 7.

The tablets had the drug release profiles shown in FIG. 6 (griseofulvin was insoluble in water, so the state of dispersion of its fine particles was evaluated by turbidity measurement). The data in FIG. 6 was obtained by conducting a release test with an apparatus of the type specified in the "Method of Disintegration Test", Japanese Pharmacopoeia, 11th rev.; 1,000 ml of distilled water was used as a testing fluid and the glass tubes containing the test fluid were moved up and down 20 times a minute.

Example 8

| Tablet | |
|---|---|
| Digoxin | 0.25 (mg) |
| Lactose | 8.75 |
| L-Cystine | 153 |
| Hydroxypropyl cellulose of low substitution degree | 120 |
| Hydroxypropyl cellulose | 15 |
| Calcium stearate | 3 |
| Total | 300 |

Digoxin (0.25 g) was dissolved in 135 g of ethanol. To the solution, 15 g of hydroxypropyl cellulose was added to make a binder solution (a film prepared by drying this solution had digoxin particles with a size of no more than 1 μm).

In the next step, 8.75 g of lactose, 153 g of L-cystine and 120 g of hydroxypropyl cellulose of low substitution degree were weighed and mixed well in a mortar. To the triturate, the separately prepared binder solution was added and blended well. The blend was granulated after passage through a 14-mesh sieve, dried at 50° C. in a tray dryer for 5 hours, and classified on a 10-mesh sieve. To 297 g of the granulation, 3 g of calcium stearate was added and the two were mixed well in a polyethylene bag.

The mix was charged into a single-punch tableting machine equipped with a die (10 mm$^\phi$) and flat-faced punches, and compressed for a total pressure of about 2 tons to make tablets each weighing 300 mg.

Figure 7:
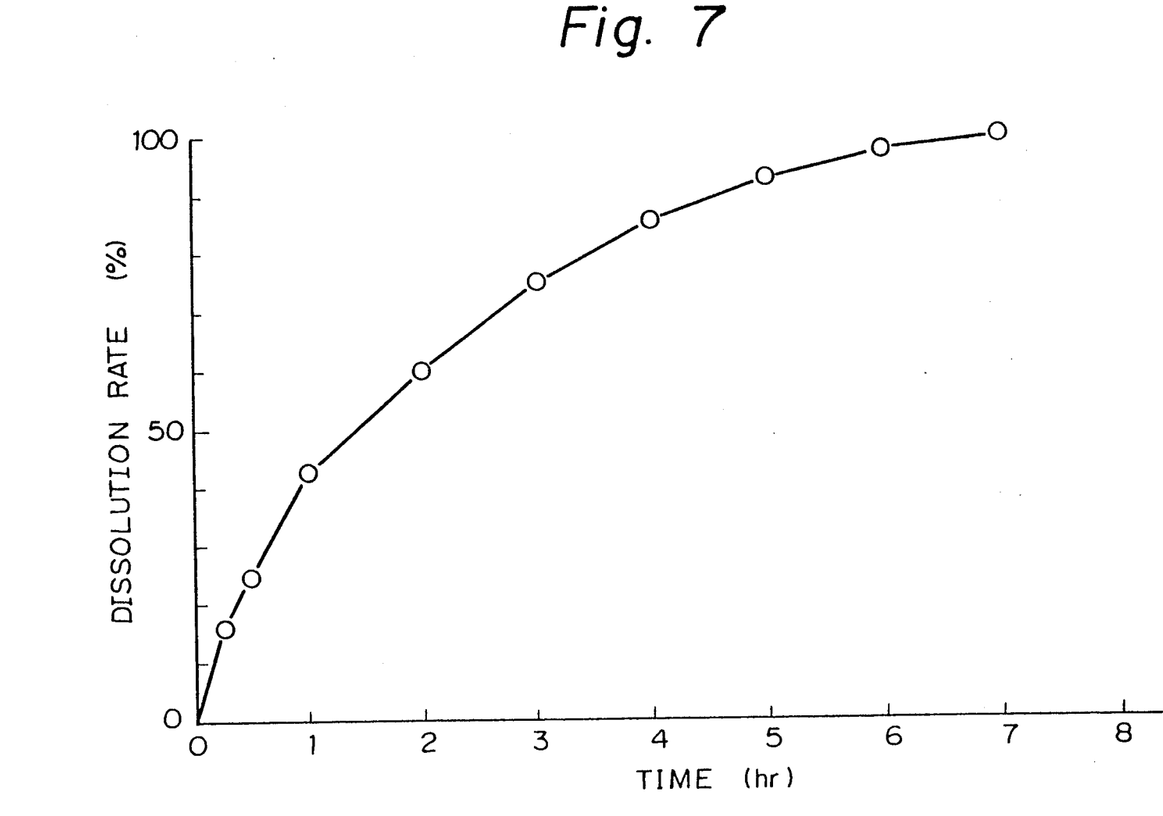
FIG. 7 depicts the dissolution profile of the tablets prepared in Example 8.

The tablets had the dissolution profiles shown in FIG. 7 that was obtained by conducting a dissolution test with an apparatus of the type described in the "Method II (puddle method) of Dissolution Test", Japanese Pharmacopoeia, 11th rev.; 900 ml of distilled water was used as a testing fluid, and the puddle was rotated at 100 rpm.

Example 9

| Tablet | |
|---|---|
| Indometacin | 25 (mg) |
| Hydroxypropyl cellulose of low substitution degree | 24 |
| Hydroxypropyl cellulose | 3 |
| L-Cystine | 92 |
| Hardened castor oil | 5 |
| Calcium stearate | 1 |
| Total | 150 |

Twenty-five grams of Indometacin (jet mill ground powder; average particle size, 6-7 μm) and 24 g of hydroxypropyl cellulose of low substitution degree were weighed and mixed well in a mortar. To the triturate, 10 g of a 10% aqueous solution of hydroxypropyl cellulose and 10 g of water were added and blended well. The blend was granulated after passage through a 24-mesh sieve, dried at 60° C. in a tray dryer for 3 hours, and classified on a 20-mesh sieve. The resulting granulation was designated granulation (a).

Ninety-two grams of L-cystine and 5 g of hardened castor oil were weighed and mixed well in a mortar. To the triturate, 20 g of a 10% aqueous solution of hydroxypropyl cellulose and 18 g of water were added and blended well. The blend was granulated after passage through a 24-mesh sieve, dried at 60° C. in a tray dryer for 3 hours, and classified on a 20-mesh sieve. The resulting granulation was designated granulation (b).

Fifty grams of granulation (a), 99 g of granulation (b) and 1 g of calcium stearate were mixed well in a polyethylene bag. The mix was charged into a single-punch tableting machine equipped with a die (8 mm$^\phi$) and flat-faced punches, and compressed for a total pressure of about 1.6 tons to make tablets each weighing 150 mg.

Figure 8:
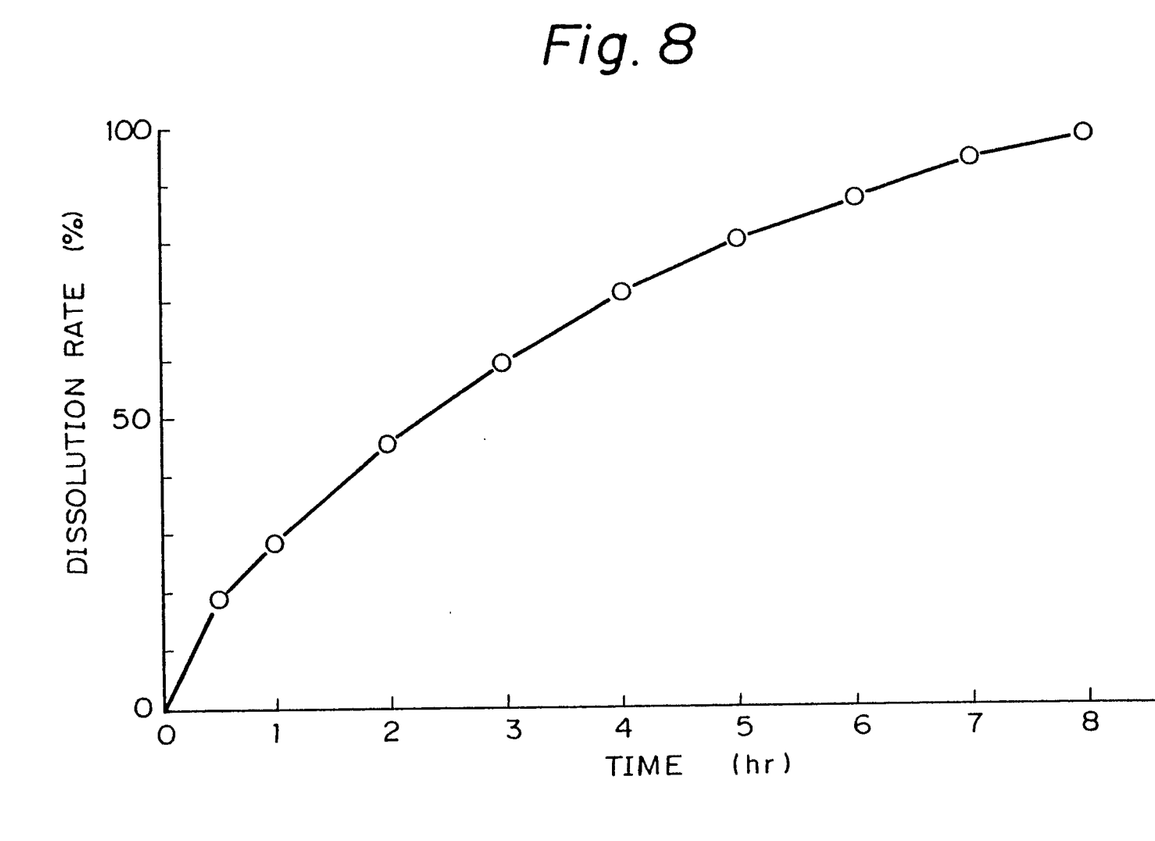
FIG. 8 depicts the dissolution profile of the tablets prepared in Example 9.

The tablets had the dissolution profiles shown in FIG. 8 that was obtained by conducting a dissolution test with an apparatus of the type specified in the "Method I (rotary basket method) of Dissolution Test", Japanese Pharmacopoeia, 11th rev.; 900 ml of Fluid 2 (pH≈6.8) was used as a testing fluid and the basket was rotated at 100 rpm.

Example 10

| Capsule | |
|---|---|
| Ketoprofen | 75 (mg) |
| L-Cystine | 49 |
| L-Tyrosine | 50 |
| Stearic acid | 20 |
| Ethyl cellulose | 6 |

Example 10-continued

| Capsule | |
|---|---|
| Total | 200 |

Seventy-five grams of Ketoprofen, 49 g of L-cystine (jet mill g round powder; average particle size, 3-4 μm), 50 g of L-tyrosine (jet mill ground powder; average particle size, 2-3 μm) and 20 g of stearic acid (jet mill g round powder; average particle size, 5-6 μm) were weighed and mixed well in a mortar. To the triturate, 60 g of a 10% solution of ethyl cellulose in ethanol was added and blended well. The blend was granulated in a rotary granulator equipped with a net (1.2 mm$^\phi$), dried at 50° C. in a tray dryer for 6 hours, and heated to about 80° C. at which temperature the granules were held for 15 minutes. The granules were then classified on a 10-mesh sieve and charged into capsules in doses of 200 mg.

Figure 9:
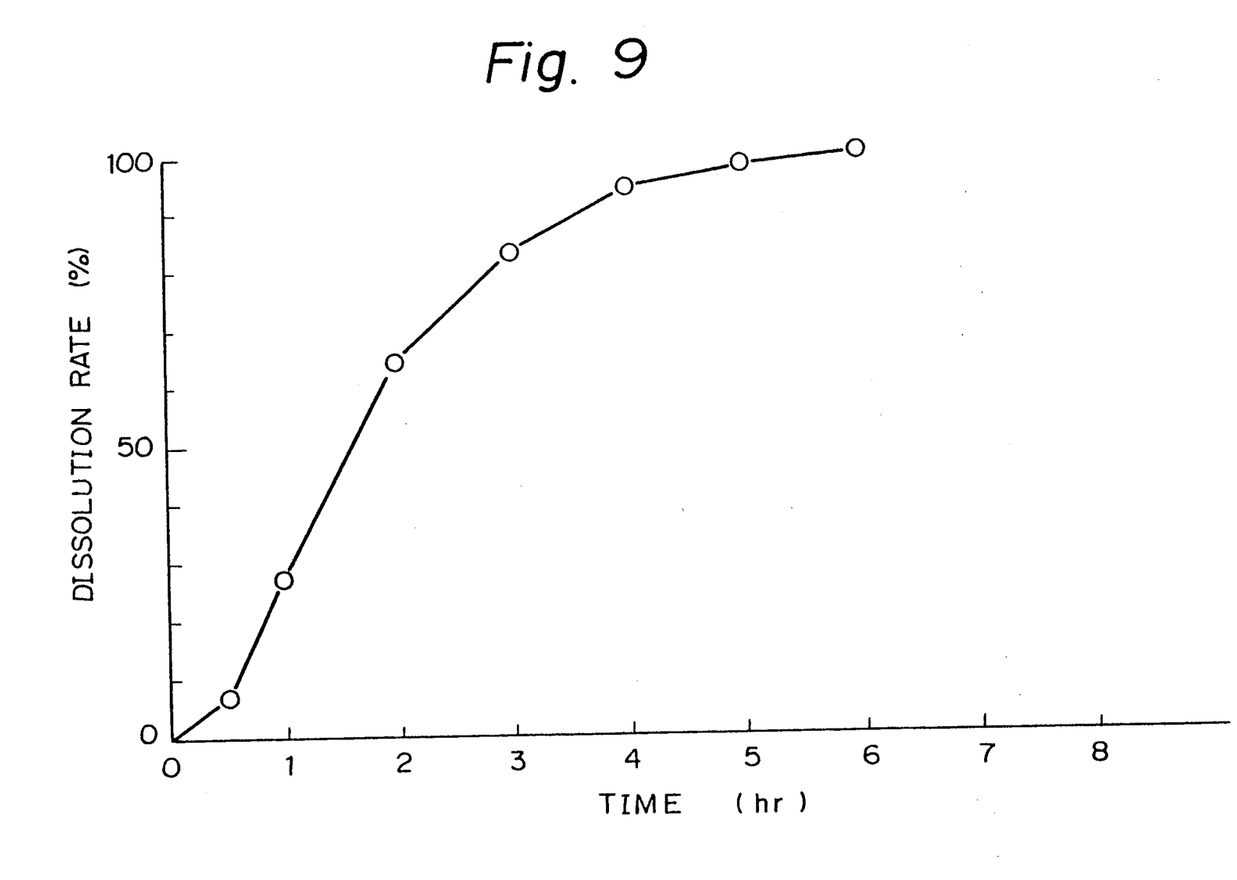
FIG. 9 depicts the dissolution profile of the capsules prepared in Example 10.

The capsules had the dissolution profile shown in FIG. 9 that was obtained by conducting a dissolution test with an apparatus of the type specified in ¢Method I (rotary basket method) of Dissolution Test", Japanese Pharmacopoeia, 11th rev.; 900 ml of Fluid 2 (pH≈6.8) was used as a testing fluid and the basket was rotated at 100 rpm.

Example 11

| Capsule | |
|---|---|
| Spherical granules | |
| Theophylline | 100 (mg) |
| Lactose | 7 |
| Crystalline cellulose | 40 |
| Hydroxypropylmethyl cellulose | 3 |
| Subtotal | 150 |
| Coating layer | |
| Ethyl cellulose | 22.5 (mg) |
| Triacetin | 2.5 |
| L-Tyrosine | 25 |
| Subtotal | 50 |
| Total | 200 |

A hundred grams of Theophylline, 7 g of lactose and 40 g of crystalline cellulose were weighed and mixed well in a mortar. To the triturate, 60 g of a 5% aqueous solution of hydroxypropylmethyl cellulose was added and blended well. The blend was granulated in a rotary granulator equipped with a net (1.0 mm$^\phi$). The granules were spheroidized with a Marumerizer machine (Model Q-236 of Fuji Powdal K.K.), and dried at 60° C. in a tray dryer for 3 hours.

Ethyl cellulose (22.5 g) and triacetin (2.5 g) were dissolved in ethanol (200 g), and 25 g of L-tyrosine (jet mill ground powder; average particle size; 2-3 μm) was dispersed with vigorous stirring to make a coating solution.

The separately prepared spherical granules (150 g) were charged into a Flow Coater (UNI-GLATT of Okawara Mfg. Co., Ltd.) and sprayed with 250 g of the coating solution. The spherical granules with a coating layer were charged into hard capsules in doses of 200 mg.

Figure 10:
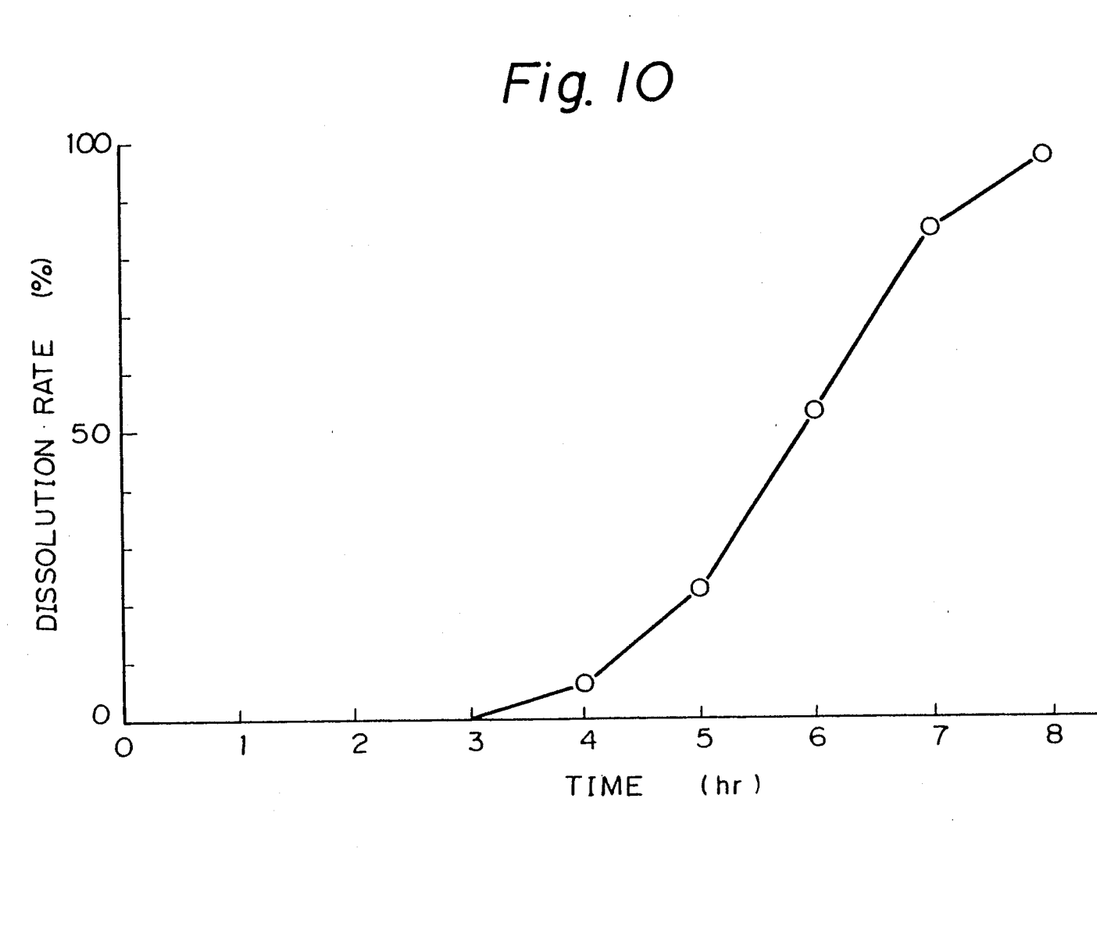
FIG. 10 depicts the dissolution profile of the capsules prepared in Example 11.

The capsules had the disolution profile shown in FIG. 10 that was obtained by conducting a dissolution test with an apparatus of the type specified in "Method I (rotary basket method) of Dissolution Test", Japanese Pharmacopoeia, 11th rev.; 500 ml of distilled water was used as a testing fluid and the basket was rotated at 100 rpm.

Example 12

| Fine granules (per gram) | |
|---|---|
| Magnesium oxide | 300 (mg) |
| L-Cystine | 320 |
| Stearic acid | 100 |
| Crystalline cellulose | 280 |
| Total | 1,000 |

Sixty grams of magnesium oxide, 64 g of L-cystine, 20 g of stearic acid and 56 g of crystalline cellulose were weighed and mixed well in a mortar. To the triturate, 80 g of water was added and blended well. The blend was granulated after passage through a 24-mesh sieve and the granulation was spheroidized with a Marumerizer machine (Model Q-234 of Fuji Powdal K.K.). The resulting fine granules were dried at 60° C. in a tray dryer for 3 hours.

Figure 11:
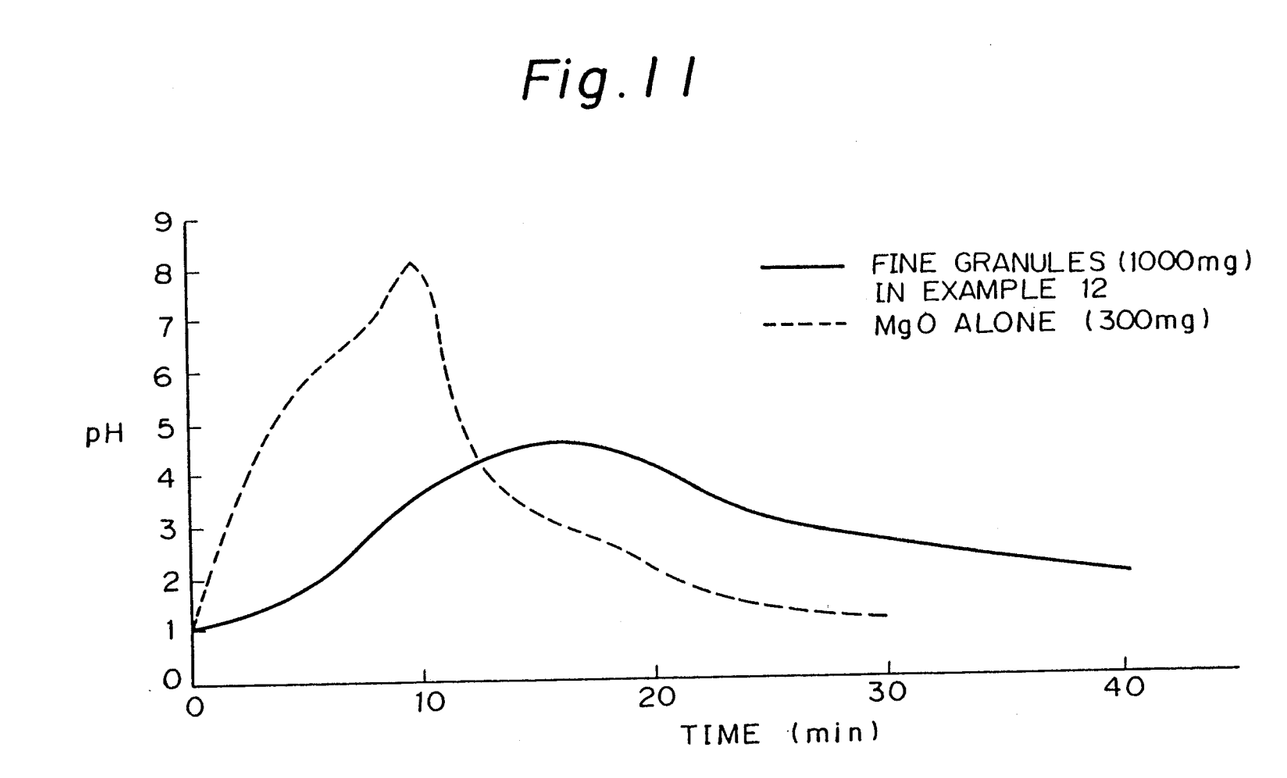
FIG. 11 shows the results of a Fuchs test conducted on the fine granules prepared in Example 12 (—0—) and MgO alone (—0—)

An acid control test (Fuchs test) was performed on these fine granules and the results are shown in FIG. 11.

Example 13

| Implant | |
|---|---|
| Erythropoietin | 0.016 (mg) |
| L-Cystine | 8.984 |
| Stearic acid | 1 |
| Total | 10 |

Figure 12:
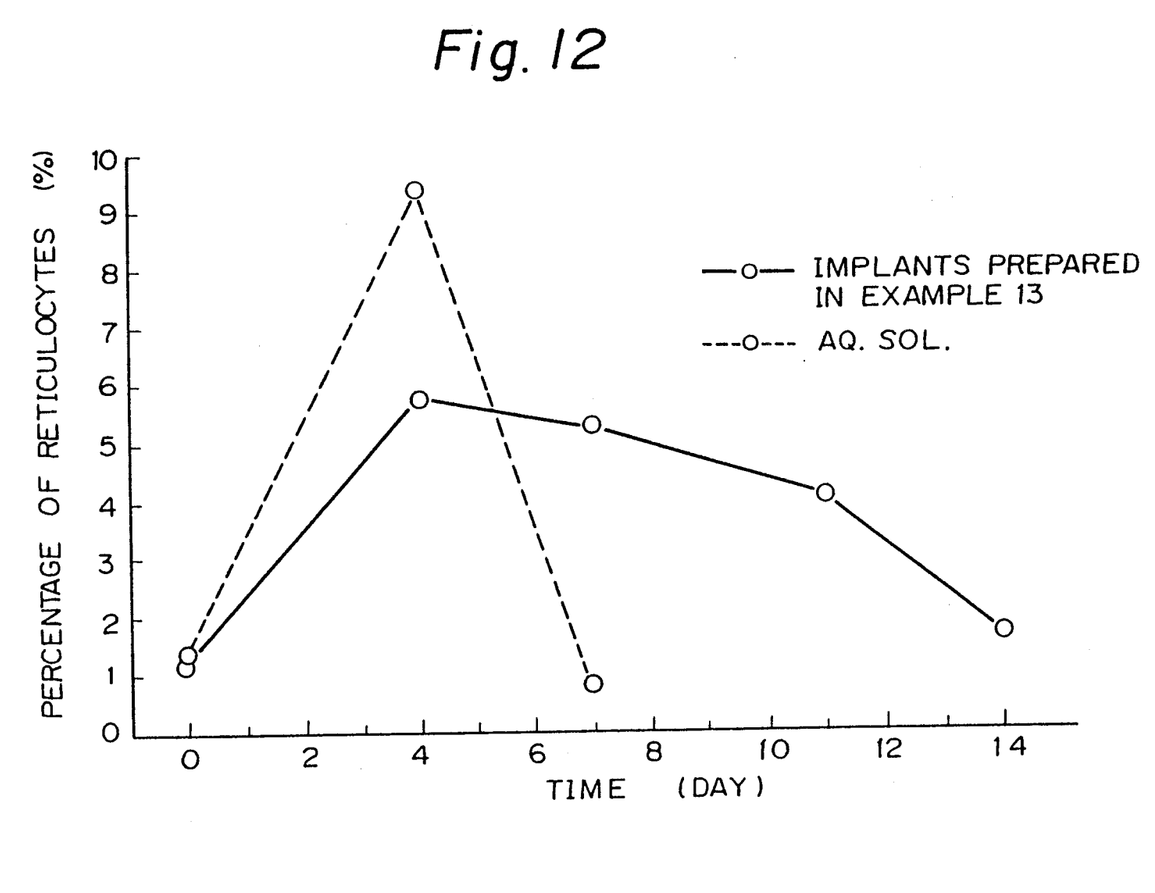
FIG. 12 shows the time-dependent change in reticulocyte counts after burial of the implants prepared in Example 13 (—) and erythropoietin in physiological saline (—).

In the first step, 0.16 mg of erythropoietin (freeze-dried), 89.84 mg of L-cystine and 10 mg of stearic acid were weighed and mixed well in a mortar. The triturate (10mg) was then charged into a mold (2 mm$^\phi$) and compressed with a hydraulic press for a total pressure of 200 kg. The so prepared implants were buried under the skin of rats and the time-dependent change in the count of reticulocytes relative to the erythrocytes in blood was examined. The results are shown in FIG. 12 together with comparative data for subcutaneous injection of erythropoietin in physiological saline.

Example 14

| Floating tablet | |
|---|---|
| Oxethazaine | 10 (mg) |
| L-Cystine | 80 |
| Stearic acid | 10 |
| Total | 100 |

One gram of Oxethazaine, 8 g of L-cystine, 1 g of stearic acid and 5 g of dl-menthol were weighed and mixed well in a mortar. The triturate was charged into a single-punch tableting machine equipped with a die (7 mm$^\phi$) and flat-faced dies, and compressed for a total pressure of about 1.5 tons to make tablets each weighing 150 mg. The tablets were heated at 50° C. under vacuum for 30 minutes to sublime dl-menthol. The tablets were further heated to 80° C. to melt the stearic acid and thereafter cooled to obtain floating tablets. When thrown into water, these tablets floated on the surface of water and remained so for at least 8 hours.

Example 15

| Troche | |
|---|---|
| Scopolamine hydrobromide | 0.2 (mg) |
| L-Cystine | 35.8 |
| DL-Tryptophan | 30 |
| Hardened castor oil | 10 |

Example 15-continued

| Troche | |
|---|---|
| Cornstarch | 3 |
| Calcium stearate | 1 |
| Total | 80 |

Two hundred milligrams of scopolamine hydrobromide, 35.8 g of L-cystine (jet mill ground powder; average particle size, 3–4 μm), 30 g of DL-tryptophan (jet mill ground powder; average particle size, 2–3 μm) and 10 g of hardened castor oil (jet mill ground powder; average particle size, 3–4 μm) were weighed and mixed well in a mortar. To the triturate, 30 g of 10% cornstarch paste was added and blended well. The blend was granulated after passage through a 14-mesh sieve, dried at 50° C. in a tray dryer for 5 hours, and classified on a 10-mesh sieve. To 79 g of the granulation, 1 g of calcium stearate was added and the two were mixed well in a polyethylene bag.

The mix was charged into a single-punch tableting machine equipped with a die (7 mm$^\phi$) and flat-faced dies, and compressed for a total pressure of about 1.5 tons to make tablets each weighing 80 mg.

The so prepared troches melted slowly in the mouth and stayed there for at least 8 hours.

What is claimed is:

1. A pharmaceutical agent in compressed which comprises at least one slow-release rendering additive of adenine, cystine and D-tyrosine in combination with at least one pharmaceutically active substance in solid particulate form, said slow-release rendering additive being in the form of particles intermixed with said at least one pharmaceutically active substance in solid particulate form.

2. A slow-release pharmaceutical agent according to claim 1 wherein the pharmaceutically active substance is a slightly soluble drug with a solubility of no more than 0.1%.

3. A slow-release pharmaceutical agent according to claim 2 wherein the slightly soluble drug is in the form of particles having an average size of no more than 10 μm.

4. A slow-release pharmaceutical agent according to claim 3 which further contains hydroxypropyl cellulose of low substitution degree and hydroxypropyl cellulose.

5. A slow-release pharmaceutical agent according to claim 1 wherein said slow-release rendering additive is adenine or cystine.

6. A slow-release pharmaceutical agent according to claim 1 wherein said slow-release rendering additive is D-tyrosine.

7. A pharmaceutical agent in granulated form, which comprises at least one slow-release rendering additive of adenine, cystine and D-tyrosine in combination with at least one pharmaceutically active substance in solid particulate form, said slow-release rendering additive being in the form of particles intermixed with said at least one pharmaceutically active substance in solid particulate form.

8. A slow-release pharmaceutical agent according to claim 1 in the form of an implant.

9. A slow-release pharmaceutical agent according to claim 1 in an encapsulated dosage form.

10. A slow-release pharmaceutical agent according to claim 1 in the form of a troche.

11. A slow-release pharmaceutical agent according to claim 1 in the form of a compacted layer of a multi-layered tablet, wherein a layer is present containing no pharmaceutically active substance.

12. A slow-release pharmaceutical agent according to claim 1 in the form of a compacted tablet, said compacted tablet being coated with a layer containing no pharmaceutically active substance.

13. A slow-release pharmaceutical agent according to claim 7 wherein the granules of said granulated from are coated with a layer containing no pharmaceutically active substance.

14. A slow-release pharmaceutical agent according to claim 1 wherein said at least one pharmaceutically active substance is selected from the group consisting of hypotensives, antipyretic analgesic antiinflammatories, immunoregulators, adrenocortical hormones, antidiabetic agents, vasodilators, cardiotonics, antiarrhythmic agents, anti-arteriosclerotic agents and antidotes.

15. A slow-release pharmaceutical agent according to claim 14 wherein said at least one pharmaceutically active substance is present in an amount less than 75% by weight of the total weight of the composition, and said slow-release rendering additive is present in amount of more than 5% by weight of the total weight of the composition.

16. A slow-release pharmaceutical agent according to claim 7 wherein said slow-release rendering additive is D-tyrosine.

17. A slow-release pharmaceutical agent according to claim 7 wherein said slow-release rendering additive is adenine or cystine.

18. A slow-release pharmaceutical solid agent which comprises at least one slow-release rendering additive of adenine, cystine and D-tyrosine in combination with at least one pharmaceutically active substance in solid particulate form, said slow-release rendering additive being in the form of particles intermixed with said at least one pharmaceutically active substance in solid particulate form.

* * * * *